(12) United States Patent
Tovena-Pecault

(10) Patent No.: US 8,291,777 B2
(45) Date of Patent: Oct. 23, 2012

(54) DEVICES FOR SAMPLING AND CONFINING CHEMICAL CONTAMINATIONS, ASSOCIATED TRANSPORT DEVICE AND APPLICATION TO THE TRANSPORT OF CHEMICAL SAMPLES TO A CHEMICAL ANALYSIS UNIT

(75) Inventor: Isabelle Tovena-Pecault, Leognan (FR)

(73) Assignee: Commissariat a l'Energie Atomique, Paris (FR)

( * ) Notice: Subject to any disclaimer, the term of this patent is extended or adjusted under 35 U.S.C. 154(b) by 538 days.

(21) Appl. No.: 12/519,145

(22) PCT Filed: Dec. 19, 2007

(86) PCT No.: PCT/EP2007/064257
§ 371 (c)(1),
(2), (4) Date: Jun. 12, 2009

(87) PCT Pub. No.: WO2008/074843
PCT Pub. Date: Jun. 26, 2008

(65) Prior Publication Data
US 2010/0031759 A1 Feb. 11, 2010

(30) Foreign Application Priority Data
Dec. 20, 2006 (FR) ...................................... 06 55724

(51) Int. Cl.
*G01N 1/22* (2006.01)
(52) U.S. Cl. .................................................. 73/863.12
(58) Field of Classification Search ................ 73/863.12
See application file for complete search history.

(56) References Cited

U.S. PATENT DOCUMENTS

| 5,509,255 A | 4/1996 | Rutledge |
| 5,669,221 A * | 9/1997 | LeBleu et al. ............. 62/92 |
| 5,765,341 A | 6/1998 | Insley et al. |
| 5,845,504 A * | 12/1998 | LeBleu ....................... 62/92 |
| 6,058,718 A * | 5/2000 | Forsberg et al. .......... 62/125 |
| 6,182,453 B1 * | 2/2001 | Forsberg ................... 62/125 |
| 2002/0083717 A1 | 7/2002 | Mullens et al. |

FOREIGN PATENT DOCUMENTS
WO   WO 02/41823 A2   5/2002

OTHER PUBLICATIONS

International Search Report for PCT/EP2007/064257 dated Feb. 20, 2008.
French Search Report for FR 0655724 dated Aug. 8, 2007.
ISO 14644-1, "Cleanrooms and associated controlled environments," AFNOR, Jul. 1999.
ISO 14644-8, "Cleanrooms and associate controlled environments," AFNOR, Nov. 2006.

* cited by examiner

*Primary Examiner* — Hezron E Williams
*Assistant Examiner* — Rodney T Frank
(74) *Attorney, Agent, or Firm* — Nixon Peabody LLP

(57) ABSTRACT

A method of sampling and confining chemical contaminations intended for the chemical analysis of contaminations in particulate and/or molecular form with prior adsorption by a support or trapping in a liquid. The adsorbent support or the contaminated liquid is then held in position in a closed box or sealed container having chemically inert walls. The outside of the closed box or sealed container is brought into contact with a gas at a higher pressure than the pressure inside the box or container and then the temperature inside the closed box or sealed container is regulated from an environment external to the gas.

18 Claims, 2 Drawing Sheets

DEVICES FOR SAMPLING AND CONFINING CHEMICAL CONTAMINATIONS, ASSOCIATED TRANSPORT DEVICE AND APPLICATION TO THE TRANSPORT OF CHEMICAL SAMPLES TO A CHEMICAL ANALYSIS UNIT

CROSS REFERENCE TO RELATED APPLICATIONS OR PRIORITY CLAIM

This application is a national phase of International Application No. PCT/EP2007/064257, entitled "DEVICES FOR SAMPLING AND CONFINING CHEMICAL CONTAMINATIONS, ASSOCIATED TRANSPORT DEVICE AND APPLICATION TO THE TRANSPORT OF CHEMICAL SAMPLES TO A CHEMICAL ANALYSIS UNIT", which was filed on Dec. 19, 2007, and which claims priority of French Patent Application No. 06 55724, filed Dec. 20, 2006.

DESCRIPTION

1. Technical Field

The invention relates to the field of ultra-cleanliness, based on materials (or nano-materials) produced in clean rooms or similar controlled environment zones.

More specifically, the invention relates to the sampling, the confinement and the transport of chemical contamination(s) likely to be found in said clean rooms or zones, with a view to an outsourced chemical analysis.

2. Prior Art

In order to minimise risks and monitor the production of materials (or nano-materials), it is necessary to analyse the contaminations likely to be present in the air of clean rooms in trace amounts or on surfaces.

However, known continuous detectors of volatile organic compounds have a current detection limit of around 0.1 ppm by volume, well above the requirements in the field of semiconductors for example, where the tolerated concentrations are less than 1 ppb by volume.

The low contamination concentrations impose in general a sampling of the compounds combined with a pre-concentration method in order to attain the detection limits required for the analyses in this field. Thus, most sampling equipment requires numerous hours of collection before being able to analyse the samples. To this time drawback may be added the risk of sample loss.

At present, there is no normalised definition of chemical contamination, even though it is currently the aim of a working group within the framework of the ISO 14644-W69 Standard.

Within the scope of the invention, it is proposed to consider chemical contamination as any particulate, molecular or ionic entity that could induce a harmful chemical reaction on a product, a patient or a method. For particulate entities, the invention preferentially applies to the confinement of particulate contaminations, of unit size between 0.1 and 5 μm for their volume shape and of unit size between 0.05 and 500 μm for their surface shape.

There do not exist either, at present, any procedures or standards enabling the chemical cleanliness of surfaces or environments to be controlled.

Nevertheless, collecting targets (in other words sampling supports) are generally used in the environments to be tested. Said sampling supports must be as representative as possible of the sensitive surfaces of the product or production method or instead offer a very large specific surface for analyses of airborne type chemical contamination.

These supports contaminated by the chemical contamination must then be confined so as:
not to lose the chemical contaminations during any transport between the sampling site and the analysis site, in other words not to modify the quantity of chemical contaminations sampled,
not to modify the chemical nature of the sampled chemical contaminations,
not to contaminate these samples by an additional contamination during transport.

DESCRIPTION OF THE INVENTION

The invention proposes overcoming the aforementioned drawbacks and thus to propose devices enabling the sampled chemical contaminations to be confined in a container or on a collection support without their nature or their quantity being modified, in particular without being contaminated by other sources of pollution.

To this end, the invention firstly relates to a device for sampling and confining chemical contaminations intended for chemical analysis, comprising:
at least one container adapted to contain a sampling liquid in which are trapped chemical contaminations in particulate and/or molecular form, the container comprising chemically inert walls,
an external envelope of dimensions adapted to maintain the sealed container in a given position and contain a gas in contact with the sealed container and at a higher pressure than inside said container, the external envelope comprising means of regulating the temperature inside the sealed container.

Within the scope of the invention, the expression "chemically inert" signifies that the considered part(s) is (are) formed of one or several materials having all of the following characteristics:
a defined degassing rate, for example, such that the total mass loss is less than 1% according to the ECSS Q70-2A test and such that the re-condensed volatile fraction is less than 0.1% according to the same test,
a defined chemical inertia, for example, such that the mass loss or gain following a potential chemical reaction is less than 1% by weight,
an aptitude to generate particles defined, for example, such that the level of surface contamination is less than a level 100 for example, according to the IEST 1246D Standard.

It goes without saying that the levels of surface particulate contamination, chemical inertia and degassing rate have to be defined but that they can be at lower or higher levels depending on the applications.

The invention also relates to a device for sampling and confining chemical contaminations intended for chemical analysis, comprising:
at least one chemical contamination sampling support adapted to adsorb contaminations in particulate and/or molecular form,
a box to maintain the support(s) in a given position, the box comprising chemically inert walls adapted to close in on themselves, forming a closed volume,
an external envelope of dimensions adapted both to envelop the closed box and to contain a gas in contact with the closed box and at a higher pressure than inside said box, the external envelope comprising means of regulating the temperature inside the closed box.

The placing of the chemical contamination bearing support(s) in the device according to the invention should preferably be carried out in a clean room (at least according to the ISO 5 Standard according to ISO 14644-1 and if possible with an ISO-AMC specificity according to ISO 14644-8) with particular precautions in the handling of the supports.

Those skilled in the art will ensure that there is a strictness (definition of procedures) in the use of the device according to the invention so as to limit the time during which said device operates in a non specified field for the contamination bearing support. The invention as defined consists in maintaining the support(s) in the device at a relatively low temperature to avoid the loss of volatile species adsorbed on the support(s) without it (them) then becoming a trap for other molecules.

The invention also relates to a transport device comprising a device for sampling and confining as previously defined, wherein the external envelope comprises a rigid part adapted to being transported manually.

The invention also relates to a method for sampling and confining chemical contaminations intended for chemical analysis comprising the following steps:

a) sampling of chemical contaminations by trapping in particulate and/or molecular form in a liquid, b) introducing the liquid containing the chemical contaminations into a container having chemically inert walls and sealing of the container, c) placing the outside of the sealed container in contact with a gas at a higher pressure than inside the container, d) regulating the temperature prevailing inside the box from an environment external to the gas.

The invention also relates to a method for sampling and confining chemical contamination(s) intended for chemical analysis comprising the following steps:

a) adsorption of chemical contaminations in particulate and/or molecular form by at least one support, b) placing the support in a rigid box having chemically inert walls and closing of the box around the support, c) bringing the outside of the closed box into contact with a gas at a higher pressure than inside the box, d) regulating the temperature prevailing inside the box from an environment external to the gas.

The sampling support adapted to the adsorption of chemical contaminations may advantageously consist in a Scotch® type adhesive or an adhesive commercialised under the trade name Tenax®.

An advantageous use of an aforementioned transport device is the transport of chemical contaminations from a production unit to a chemical analysis unit.

BRIEF DESCRIPTION OF DRAWINGS

Other advantages and characteristics will become more apparent on reading the following figures, in which.

DETAILED DESCRIPTION OF SPECIFIC EMBODIMENTS

Figure 1:
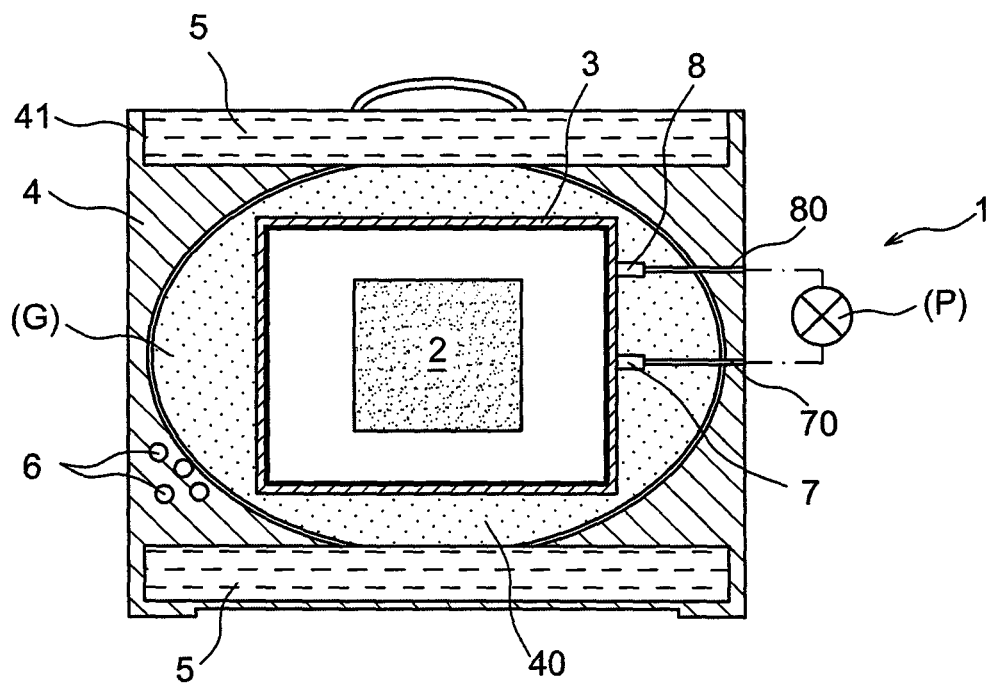
FIG. 1 is a general schematic view of a preferred embodiment of a device according to the invention.
Figure 1A:
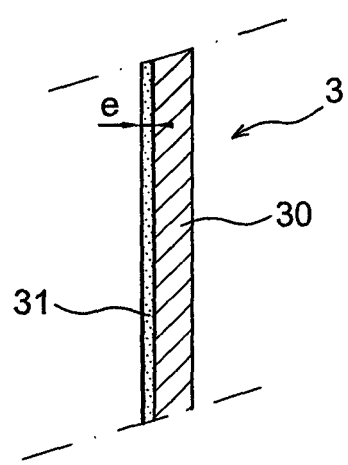
FIG. 1a is an enlarged view of a part of FIG. 1 showing the constitution of a box according to the invention.

The suitcase illustrated incorporates a device for sampling and confining 1 according to the invention.

Said device 1 firstly comprises:

a support 2 on which chemical contaminations sampled on a production line have been adsorbed, a box 3 closed around the support 2. By way of example, the walls 30 of this box 3 are here made of stainless steel, the faces 300 opposite the support 2 being coated with a layer 31 of Teflon®. Preferably, the thickness (e) of the layer 31 is around ten or so microns.

Figure 2:
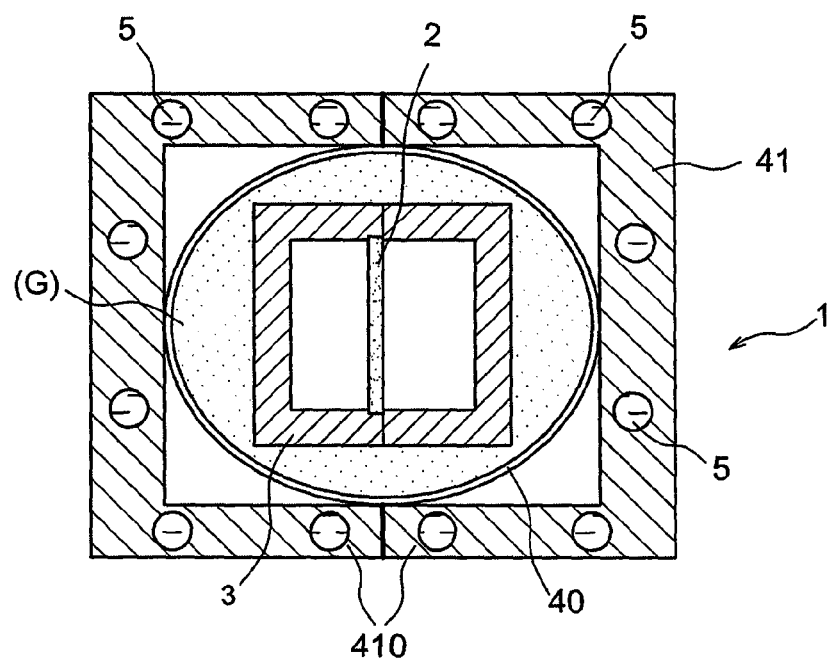
FIG. 2 is a transversal sectional view along the axis of symmetry of the device of FIG. 1.
Figure 2A:
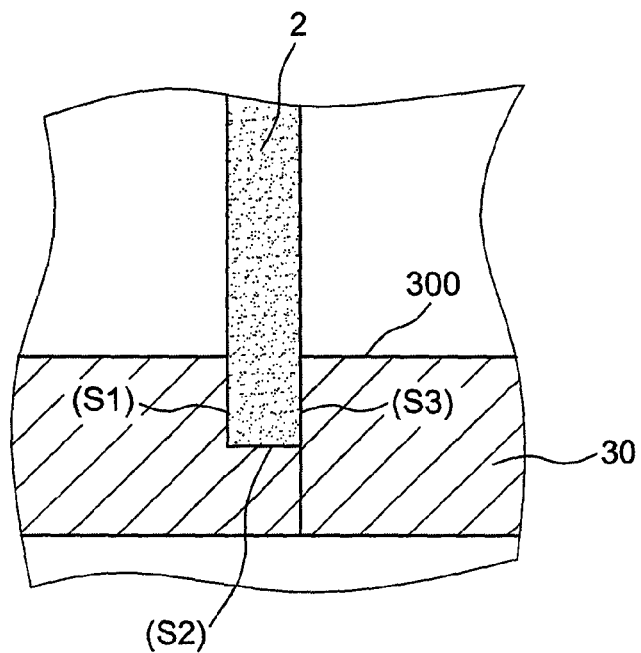
FIG. 2a is an enlarged view of FIG. 2 showing a contact zone between the support and the box according to the invention.

As may be seen in FIG. 2A, the box 3 is adjusted to maintain the support 2 in a given position, the contact surface (S1+S2+S3) between the support 2 and the box 3 being judiciously chosen to be very low with regard to the dimensions of the support 2. The Teflon® advantageously deposited on the contact surfaces (S1), (S2) and (S3) makes it possible to limit the transfer of the chemical contamination from the contaminated support 2 to the box 3.

The device 1 also comprises an external envelope 4, a flexible part 40 of which is inflated around the closed box 3 containing the chemical contaminations support 2 (FIG. 2). This flexible part 40 is inflated with an inert gas (G) at a higher pressure than inside the box 3 and comprises a chemically inert film and makes it possible in particular to avoid the subsequent introduction of particulate contaminations. Preferably, the film is made of natural polyethylene with low degassing rate and mechanically resistant. Alternative embodiments to be envisaged may consist in inflating the flexible part 40 (for example, a bag or sealed film made of chemically inert plastic) by means of an inert gas or not, containing desiccants or not.

The external envelope 4 also comprises a rigid part 41 comprising two suitcase flaps 410. Inside said flaps 410 is implanted a chilled water circuit 5, which makes it possible to maintain a lower temperature, preferably of at least 5° C., than the operating temperature of the contaminated support. By way of example, when the operating temperature is around 21° C. (typically the temperature of a clean room), the chilled temperature chosen will be preferentially around 15° C.

The rigid part 41 also comprises means of regulating (6) the hygrometry, here in the form of desiccants (FIG. 1).

The rigid part 41 of the suitcase thus maintains controlled conditions of temperature and hygrometry limiting the desorption of the chemical contamination deposited on the samples.

It goes without saying that as an alternative to the means of regulating the temperature, eutectics may be chosen, the volume of which depend on the desired temperature and the time this temperature is maintained.

Preferably, the box 3 must be able to be cleaned or maintained in an inert gas, which leads to the associated injection system, as represented in FIG. 1: references 7,70. This injection system enables the box 3 to be connected to a filtered inert gas system (P) for a cleaning before introduction of support(s) 2. Moreover, the box 3 comprises an ejection nozzle 8 in which is incorporated a particulate filter, the ejection nozzle 8 being connected to the outside of the envelope 4 by a channel 80 so as to be able to eject any residual gas from the contaminated support 2 to be analysed, residual gas present inside the closed box 3 containing the support (2). The filters used, not represented, will preferably be chosen to be able to recover the collecting membranes of the particulate part of the chemical contamination.

The invention thus proposes a reliable means that makes it possible to guarantee the confinement of chemical contamination(s), in particular in gaseous form, on a support while advantageously controlling the parameters of temperature and hygrometry surrounding said support.

The invention thus disclosed makes it possible:

- to maintain the chemical contamination(s) on a support without loss and without denaturing either the support or the chemical contamination, whether in molecular form or in particulate form,
- to guarantee the confinement of the chemical contamination(s) on the sampling support vis-à-vis the exterior by a multi-barrier concept,
- to guarantee the chemical and mechanical inertia of the confinement box compared to the chemical contamination(s) deposited on the liquid or solid support,
- to maintain the temperature of the support at temperatures below the usual temperature to avoid the desorption of the molecules condensed on the support,
- to maintain the hygrometry at contents representative of the conditions of use of the contaminated surface,
- to clean the confinement box before execution by a purge with filtered inert gas,
- to limit the losses of chemical contamination by a higher pressure of inert gas around the confinement box,
- to avoid the additive generation of particles or molecules during transport, by means of a judicious selection of the materials constituting the barriers (box, external envelope, and, if necessary, flexible envelope), these materials having low degassing rates and low potentials to generate particles.

The immediate and future applications targeted by the invention are numerous: in certain industries (in the space field, micromechanics, optics, nanotechnologies but also the pharmaceuticals and food processing industries, hospitals, etc.), the control of chemical contamination entails samplings on solid or liquid supports on the process line. On the other hand, few industries have their own chemical analysis laboratory. Consequently, it is essential to have available reliable means of transporting these samples.

The invention can also just as easily apply to the confinement and transport of bio-contamination, such as that defined in the ISO 14698-1 Standard, for example bacteria, fungi, parasites or viruses.

The invention claimed is:

1. Device for sampling and confining chemical contaminations intended for chemical analysis, comprising:
    at least one sealed container adapted to contain a sampling liquid in which are trapped chemical contaminations in particulate and/or molecular form, the container comprising chemically inert walls,
    an external envelope of dimensions adapted to maintain the sealed container in a given position and to contain a gas in contact with the sealed container and at a higher pressure than inside said sealed container, the external envelope comprising means of regulating the temperature inside the sealed container.

2. Device for sampling and confining according to claim 1, wherein the means of regulating the temperature comprise a chilled water circuit.

3. Device for sampling and confining according to claim 1, wherein a temperature probe is implanted inside the closed box around the support or the sealed container in order to display the T° from the environment outside the envelope and to regulate it manually.

4. Device for sampling and confining according to claim 1, wherein the gas contained within the external envelope and in contact with the closed box or the sealed container is an inert gas.

5. Transport device comprising a device for sampling and confining according to claim 1, wherein the external envelope comprises a rigid part adapted to be manually transported.

6. Transport device according to claim 5, wherein the external envelope comprises suitcase flaps.

7. Use of the transport device according to claim 5 for the transport of chemical contaminations from a production unit to a chemical analysis unit.

8. Device for sampling and confining chemical contaminations intended for chemical analysis, comprising:
    at least one support adapted to adsorb chemical contaminations in particulate and/or molecular form,
    a closed box to maintain the support(s) in a given position, the box comprising chemically inert walls adapted to close in on themselves, forming a closed volume,
    an external envelope of dimensions adapted both to envelope the closed box and to contain a gas in contact with the closed box and at a higher pressure than inside said closed box, the external envelope comprising means of regulating the temperature inside the closed box.

9. Device for sampling and confining according to claim 8, wherein the external envelope comprises a flexible chemically inert part, with dimensions adapted both to envelop the closed box and to contain a gas in contact with the closed box and at a higher pressure than inside said box.

10. Device for sampling and confining according to claim 9, wherein the flexible part is a polyethylene film.

11. Device for sampling and confining according to claim 8, wherein the envelope comprises means of regulating the hygrometry.

12. Device for sampling and confining according to claim 11, wherein the means of regulating the hygrometry comprise desiccants, such as beads of silica-gel, $CaCl_2$.

13. Device for sampling and confining according to claim 8, wherein the walls of the box are made of stainless steel and its faces opposite the support are covered with a chemically inert coating such as Teflon.

14. Device for sampling and confining according to claim 8, comprising an injection nozzle in which is incorporated a particulate filter, the injection nozzle passing through the box and being linked to the outside of the envelope by a channel so as to be able to inject an inert gas inside the closed box containing the support.

15. Device for sampling and confining according to claim 8, comprising an ejection nozzle in which is incorporated a particulate filter, the ejection nozzle being linked to the outside of the envelope by a channel so as to be able to eject any residual gas present inside the closed box containing the support.

16. Method for sampling and confining chemical contaminations intended for chemical analysis comprising the following steps:
    a) sampling of chemical contaminations by trapping in particulate and/or molecular form in a liquid,
    b) introducing the liquid containing the chemical contaminations into a container having chemically inert walls and sealing of the container,
    c) bringing the outside of the sealed container into contact with a gas at a higher pressure than inside the container,
    d) regulating the temperature prevailing inside the sealed container from an environment external to the gas.

17. Method of sampling and confining chemical contamination(s) according to claim 16, wherein the gas at higher pressure is an inert gas.

18. Method for sampling and confining chemical contaminations intended for chemical analysis comprising the following steps:
    a) adsorption of the chemical contaminations in particulate and/or molecular form by at least one support, b) placing the support in a box having chemically inert walls and closing of the box around the support,
c) bringing the outside of the closed box into contact with a gas at a higher pressure than inside the box,
d) regulating the temperature prevailing inside the closed box from an environment external to the gas.

* * * * *